United States Patent [19]

Inoue et al.

[11] Patent Number: 5,574,800
[45] Date of Patent: Nov. 12, 1996

[54] PATTERN DEFECT INSPECTION METHOD AND APPARATUS

[75] Inventors: Hiromu Inoue; Kentaro Okuda, both of Yokohama, Japan

[73] Assignee: Kabushiki Kaisha Toshiba, Kawasaki, Japan

[21] Appl. No.: 294,510

[22] Filed: Aug. 23, 1994

[30] Foreign Application Priority Data

Aug. 24, 1993 [JP] Japan .................................. 5-209453

[51] Int. Cl.6 .................................................... G06K 9/00
[52] U.S. Cl. .......................... 382/149; 382/199; 382/205
[58] Field of Search ............................... 382/8, 22, 30, 382/34, 141, 199, 209, 218, 205; 348/86, 92, 125, 126, 129, 130; 356/394

[56] References Cited

U.S. PATENT DOCUMENTS

| | | |
|---|---|---|
| 4,532,650 | 7/1985 | Wihl et al. . |
| 4,805,123 | 2/1989 | Specht et al. . |
| 4,958,374 | 9/1990 | Tokita et al. .................... 382/8 |
| 5,146,509 | 9/1992 | Hara et al. .................... 382/8 |
| 5,157,735 | 10/1992 | Maeda et al. .................... 382/8 |
| 5,185,812 | 2/1993 | Yamashita et al. .................... 382/8 |

FOREIGN PATENT DOCUMENTS

| | | |
|---|---|---|
| 62-266406 | 11/1987 | Japan . |
| 3-292752 | 12/1991 | Japan . |
| 4-363045 | 12/1992 | Japan . |
| 2102122 | 1/1983 | United Kingdom . |

*Primary Examiner*—Joseph Mancuso
*Attorney, Agent, or Firm*—Finnegan, Henderson, Farabow, Garrett & Dunner, L.L.P.

[57] ABSTRACT

The pattern edge direction in reference image data of an object to be examined is detected, the reference image data is differentiated using a differential operator in a direction along the pattern edge direction, and inspection image data obtained by picking up an image of the object to be inspected is differentiated using the differential operator in the direction along the pattern edge direction. The differential data obtained by the differential processing are compared with the inspection image data, and a pattern defect on the object to be inspected is detected based on the difference between these data.

14 Claims, 15 Drawing Sheets

| 0 | 0 | 0 |
|---|---|---|
| -1 | 0 | 1 |
| 0 | 0 | 0 |

~Da

X DIRECTION

| 0 | 1 | 0 |
|---|---|---|
| 0 | 0 | 0 |
| 0 | -1 | 0 |

~Db

Y DIRECTION

| 0 | 0 | 1 |
|---|---|---|
| 0 | 0 | 0 |
| -1 | 0 | 0 |

~Dc

+45° DIRECTION

| -1 | 0 | 0 |
|---|---|---|
| 0 | 0 | 0 |
| 0 | 0 | 1 |

~Dd

-45° DIRECTION

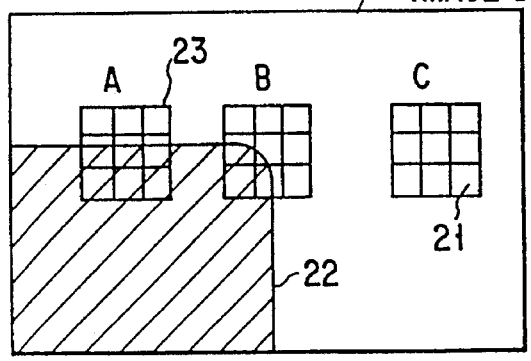
FIG. 3
FIG. 4
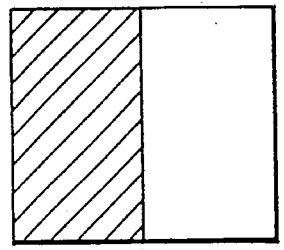
FIG. 5
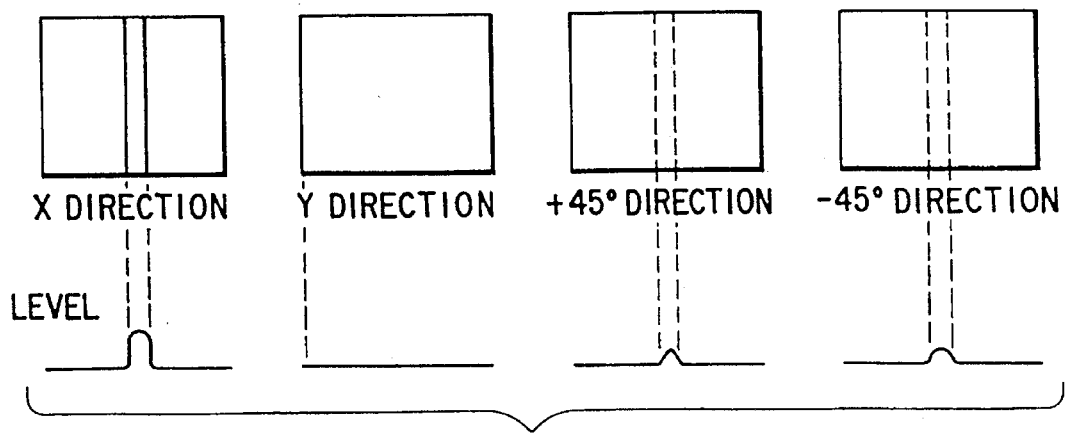
FIG. 6

X DIRECTION

Y DIRECTION

+45° DIRECTION

-45° DIRECTION

UNIFORM PORTION

EDGE PORTION

PIXEL DATA
(POSITION A)

| 10 | 10 | 10 | 10 | 10 |
|----|----|----|----|----|
| 7  | 7  | 7  | 7  | 7  |
| 5  | 5  | 5  | 5  | 5  |
| 3  | 3  | 3  | 3  | 3  |
| 0  | 0  | 0  | 0  | 0  |

CENTRAL PIXEL DATA

| 0 | 0 | 0 |
|---|---|---|
| 0 | 0 | 0 |
| 0 | 0 | 0 |

DIFFERENTIAL VALUE IN X DIRECTION

| 5 | 5 | 5 |
|---|---|---|
| 4 | 4 | 4 |
| 5 | 5 | 5 |

DIFFERENTIAL VALUE IN Y DIRECTION

| 5 | 5 | 5 |
|---|---|---|
| 4 | 4 | 4 |
| 5 | 5 | 5 |

DIFFERENTIAL VALUE IN +45° DIRECTION

| -5 | -5 | -5 |
|----|----|----|
| -4 | -4 | -4 |
| -5 | -5 | -5 |

DIFFERENTIAL VALUE IN -45° DIRECTION

F I G.  12

| | | | | |
|---|---|---|---|---|
| 10 | 10 | 10 | 10 | 10 |
| 7 | 7 | 7 | 7 | 7 |
| 5 | 5 | 5 | 5 | 5 |
| 3 | 3 | 3 | 3 | 3 |
| 0 | 0 | 0 | 0 | 0 |

PIXEL DATA (POSITION A)

⟹ MINIMUM VALUE DIRECTION (X DIRECTION)

EDGE PORTION

| | | 38 |
|---|---|---|
| 0 | 0 | 0 |
| 0 | 0 | 0 — 37a |
| 0 | 0 | 0 |

DIFFERENTIAL ABSOLUTE VALUE (MINIMUM DIRECTION)

⌈0⌋ MAXIMUM DIFFERENTIAL VALUE

FIG. 13A

| | | | | |
|---|---|---|---|---|
| 10 | 10 | 10 | 10 | 10 |
| 7 | 7 | 7 | 8 | 10 |
| 5 | 5 | 6 | 7 | 10 |
| 3 | 4 | 5 | 7 | 10 |
| 0 | 3 | 5 | 7 | 10 |

PIXEL DATA (POSITION B)

⇖ MINIMUM VALUE DIRECTION (-45° DIRECTION)

(-45°) CORNER PORTION

| | | |
|---|---|---|
| 4 | 3 | 0 — 37c |
| 2 | 0 | 3 |
| 0 | 2 | 4 |

DIFFERENTIAL ABSOLUTE VALUE (MINIMUM DIRECTION)

⌈4⌋ MAXIMUM DIFFERENTIAL VALUE

FIG. 13B

| | | | | |
|---|---|---|---|---|
| 0 | 0 | 0 | 0 | 0 |
| 0 | 0 | 0 | 0 | 0 |
| 0 | 0 | 0 | 0 | 0 |
| 0 | 0 | 0 | 0 | 0 |
| 0 | 0 | 0 | 0 | 0 |

PIXEL DATA (POSITION C)

UNDECIDED MINIMUM VALUE DIRECTION

| | | |
|---|---|---|
| 0 | 0 | 0 |
| 0 | 0 | 0 |
| 0 | 0 | 0 |

DIFFERENTIAL ABSOLUTE VALUE (MINIMUM DIRECTION)

⌈0⌋ MAXIMUM DIFFERENTIAL VALUE

FIG. 13C

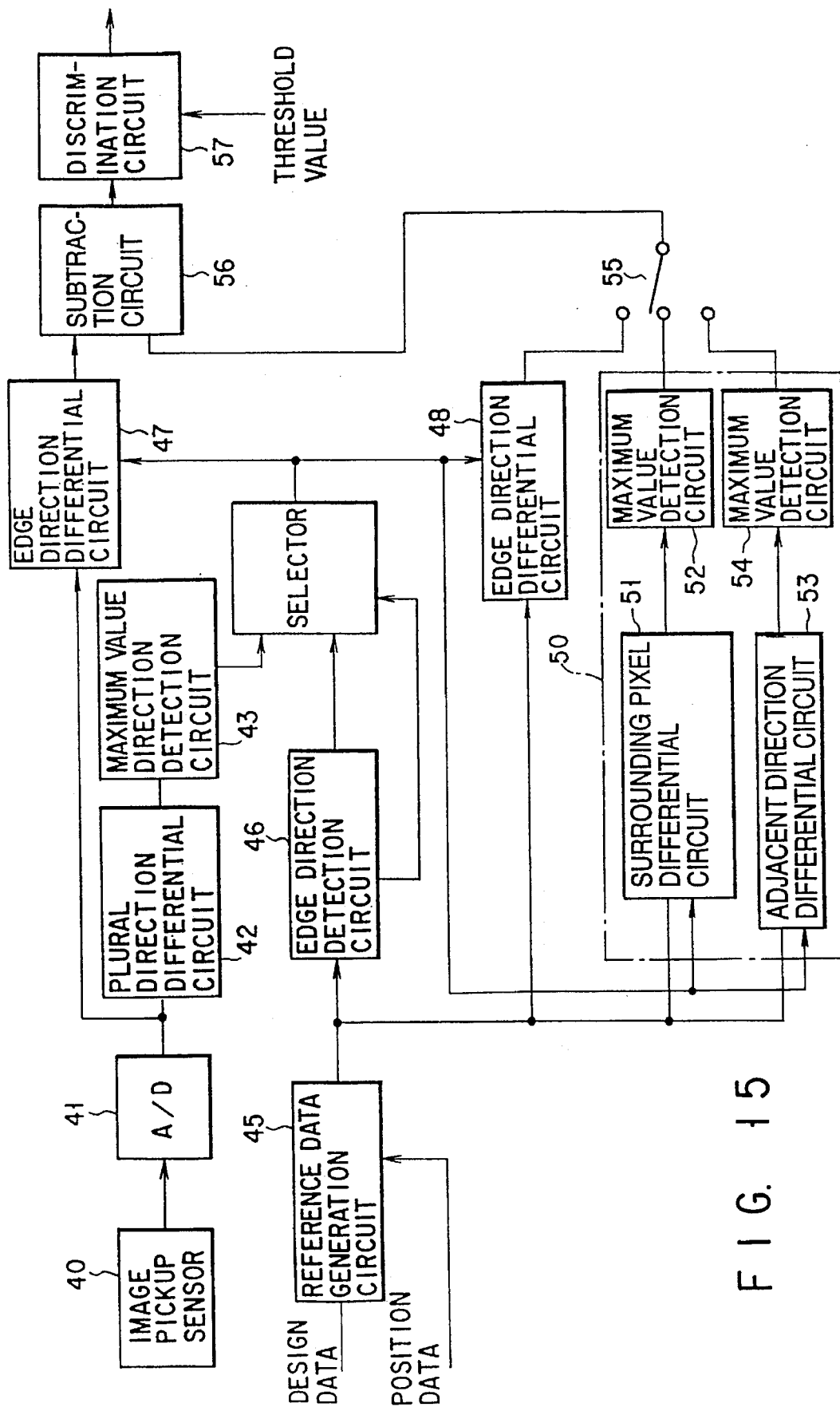
F I G. 15

| 0 | 0 | 1/2 |
|---|---|---|
| -1/2 | 0 | 1/2 |
| -1/2 | 0 | 0 |

+22.5° DIRECTION

| 0 | 1/2 | 1/2 |
|---|---|---|
| 0 | 0 | 0 |
| -1/2 | -1/2 | 0 |

+67.5 DIRECTION

| -1/2 | 0 | 0 |
|---|---|---|
| -1/2 | 0 | 1/2 |
| 0 | 0 | 1/2 |

-22.5° DIRECTION

| -1/2 | -1/2 | 0 |
|---|---|---|
| 0 | 0 | 0 |
| 0 | 1/2 | 1/2 |

+67.5 DIRECTION a EDGE PORTION

```
┌─────────────────────┐
│10 10 10 10 10 10 10 │
│10┌───────────┐10    │
│10│10 10 10 10 10│10 │
│ 8│ 8  8  8  8  8│ 8 │
│ 5│ 5  5  5  5  5│ 5 │
│ 2│ 2  2  2  2  2│ 2 │
│ 0│ 0  0  0  0  0│ 0 │
│  └───────────┘      │
│ 0  0  0  0  0  0  0 │
└─────────────────────┘
``` b CORNER PORTION

```
┌─────────────────────┐
│10 10 10 10 10 10 10 │
│10┌───────────┐10    │
│10│10 10 10 10 10│10 │
│ 8│ 8  8  9 10 10│10 │
│ 5│ 5  6  7  9 10│10 │
│ 2│ 2  4  6  8 10│10 │
│ 0│ 0  2  5  8 10│10 │
│  └───────────┘      │
│ 0  0  2  5  8 10 10 │
└─────────────────────┘
``` c UNIFORM PORTION

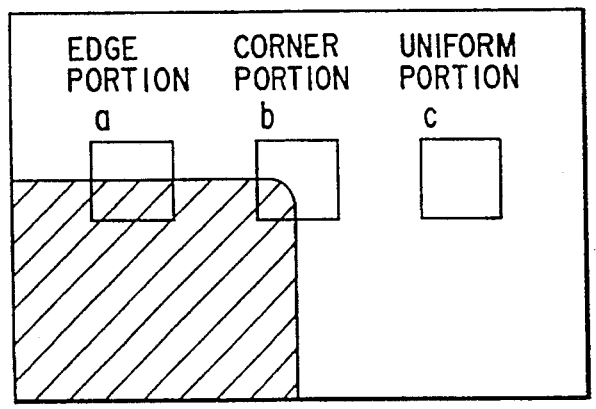

FIG. 19 a EDGE PORTION

```
10 10 10  9  9
 8  8  7  8  8
 5  4  5  5  5
 2  1  1  2  2
 0  0  0  1  0
``` b CORNER PORTION

```
 8  9  9 10 10
 5  5  7  8 10
 2  3  6  8 10
 0  2  4  7  9
 1  2  5  7 10
``` c UNIFORM PORTION

```
10 10 10 10  9
10 10  9 10 10
10 10 10 10 10
10  9 10 10 10
10 10 10 10 10
```

FIG. 20 a EDGE PORTION / b CORNER PORTION / c UNIFORM PORTION

FIG. 25A EDGE DIRECTION

FIG. 25B SURROUNDING PIXEL

FIG. 25C ADJACENT DIRECTION

|   |   |   |
|---|---|---|
| 1 | 0 | 1 |
| 0 | 1 | 0 |
| 1 | 1 | 1 |

EDGE DIRECTION

FIG. 26A

|   |   |   |
|---|---|---|
| 1 | 0 | 1 |
| 0 | 1 | 0 |
| 1 | 1 | 1 |

SURROUNDING PIXEL

FIG. 26B

|   |   |   |
|---|---|---|
| 0 | 0 | 0 |
| 0 | 0 | 0 |
| 0 | 0 | 0 |

ADJACENT DIRECTION

FIG. 26C

|   |   |   |
|---|---|---|
| 5 | 1 | 5 |
| 4 | 1 | 4 |
| 1 | 1 | 1 |

EDGE DIRECTION

FIG. 27A

|   |   |   |
|---|---|---|
| 5 | 1 | 5 |
| 4 | 1 | 4 |
| 1 | 1 | 1 |

SURROUNDING PIXEL

FIG. 27B

|   |   |   |
|---|---|---|
| 3 | 0 | 3 |
| 1 | 0 | 1 |
| 0 | 0 | 0 |

ADJACENT DIRECTION

FIG. 27C

|   |   |   |
|---|---|---|
| — | \ | \ |
| — | \ | \ |
| \ | \| | \| |

FIG. 28

|   |   |   |
|---|---|---|
| 2 | 1 | 1 |
| 4 | 2 | 2 |
| 3 | 1 | 1 |

FIG. 29A

|   |   |   |
|---|---|---|
| 4 | 1 | 1 |
| 7 | 2 | 1 |
| 3 | 4 | 3 |

FIG. 29B

| 1 | 1 | 0 |
|---|---|---|
| 2 | 0 | 1 |
| 0 | 2 | 1 |

EDGE
DIRECTION

FIG. 30A

| 3 | 3 | 1 |
|---|---|---|
| 4 | 3 | 3 |
| 4 | 4 | 3 |

SURROUNDING
PIXEL

FIG. 30B

| 3 | 2 | 0 |
|---|---|---|
| 4 | 1 | 2 |
| 2 | 4 | 3 |

ADJACENT
DIRECTION

FIG. 30C

SUBTRACTION
RESULT
WITHOUT
DEFECT

| 1 | 0 | 1 |
|---|---|---|
| 2 | 2 | 1 |
| 3 | 0 | 0 |

EDGE
DIRECTION

FIG. 31A

| 0 | 0 | 0 |
|---|---|---|
| 0 | 0 | 0 |
| 0 | 0 | 0 |

SURROUNDING
PIXEL

FIG. 31B

| 0 | 0 | 1 |
|---|---|---|
| 0 | 1 | 0 |
| 1 | 0 | 0 |

ADJACENT
DIRECTION

FIG. 31C

SUBTRACTION
RESULT
WITH
DEFECT

| 3 | 0 | 1 |
|---|---|---|
| 5 | 2 | 0 |
| 3 | 2 | 2 |

EDGE
DIRECTION

FIG. 32A

| 1 | 0 | 0 |
|---|---|---|
| 3 | 0 | 0 |
| 0 | 0 | 0 |

SURROUNDING
PIXEL

FIG. 32B

| 1 | 0 | 1 |
|---|---|---|
| 3 | 1 | 0 |
| 1 | 0 | 0 |

ADJACENT
DIRECTION

EDGE
DIRECTION

SURROUNDING
PIXEL

ADJACENT
DIRECTION

|   |   |   |
|---|---|---|
| 1 | 0 | 1 |
| 1 | 1 | 1 |
| 0 | 1 | 0 |

FIG. 36

|   |   |   |
|---|---|---|
| 5 | 5 | 5 |
| 5 | 1 | 5 |
| 5 | 5 | 5 |

FIG. 37

|    |   |   |
|----|---|---|
| -1 | 0 | 1 |
| -2 | 0 | 2 |
| -1 | 0 | 1 | x DIRECTION

FIG. 38A

|    |    |    |
|----|----|----|
| 1  | 2  | 1  |
| 0  | 0  | 0  |
| -1 | -2 | -1 | y DIRECTION

FIG. 38B

|    |    |   |
|----|----|---|
| 0  | 1  | 2 |
| -1 | 0  | 1 |
| -2 | -1 | 0 |

+45° DIRECTION

FIG. 38C

|    |    |   |
|----|----|---|
| -2 | -1 | 0 |
| -1 | 0  | 1 |
| 0  | 1  | 2 |

-45° DIRECTION

FIG. 38D

PATTERN DEFECT INSPECTION METHOD AND APPARATUS

BACKGROUND OF THE INVENTION

1. Field of the Invention

The present invention relates to a pattern defect inspection method and apparatus for detecting a defect of an object to be inspected by comparing reference image data and inspection image data obtained by optically scanning the object to be inspected.

2. Description of the Related Art

For example, the inspection process of semiconductor masks or printed circuit boards in a semiconductor manufacturing factory is needed for guarantee the quality of the product. In this inspection process, it must be inspected whether or not a pattern on a manufactured semiconductor mask or printed circuit board coincides with a design pattern.

This automatic inspection process is performed as follows.

An inspection pattern on a semiconductor mask or a printed circuit board as an object to be measured is read by an image sensor to obtain two-dimensional inspection image data.

It is checked if the inspection image data coincides with reference image data of a reference pattern obtained from design data.

As a result of this checking, if the inspection image data does not coincide with the reference pattern, a defect signal is output, and a defect position on the inspection pattern is specified.

FIG. 1 is a block diagram of such a pattern defect inspection apparatus.

An image sensor 1 scans an object to be inspected, and outputs the image signal. The image signal is converted into digital multi-value data corresponding to, e.g., 11 density levels "0" to "10" by an A/D converter 2.

With this conversion, two-dimensional inspection image data is generated. The inspection image data corresponds to an inspection pattern on the object to be inspected, and is supplied to a first differential circuit 3.

The first differential circuit 3 has differential operators respectively in x (horizontal), y (vertical), +45°, and −45° directions shown in FIGS. 2A to 2D.

The x and y directions are orthogonal directions. The ±45° directions define angles with respect to the x direction.

The first differential circuit 3 spatially differentiates the inspection image data using these differential operators in the four differential directions, and sends differential results to a selector 4.

On the other hand, a design data memory 5 stores a design data pattern generated based on design data of the pattern to be formed on the inspected object.

A reference image generator 6 converts the design data of the design data pattern into digital multi-value data corresponding to, e.g., 11 density levels "0" to "10", and supplies the conversion result to a second differential circuit 7 as reference image data.

The second differential circuit 7 has the same differential operators as in the first differential circuit 3, i.e., differential operators respectively in the x (horizontal), y (vertical), +45°, and −45° directions.

The second differential circuit 7 spatially differentiates the reference image data using these four differential operators, and sends differential results to a minimum value direction detection circuit 8.

A case will be exemplified below wherein the inspection image data is as shown in FIG. 3.

Inspection image data 20 (FIG. 3) is composed of pixel data 21 of a plurality of pixels. A pattern 22 is defined by the respective level values of these pixel data 21.

Each of local areas 23 is defined by 3×3, i.e., a total of nine pixel data 21.

Of these areas, the local area 23 at a position A is located at an edge portion of the pattern 22. The local area 23 at a position B is located at a corner portion of the pattern 22. The local area at a position C is located at a uniform portion other than the pattern 22.

For example, pixel data in the local area 23 at the position A has a smooth density gradation, as shown in FIG. 4. This local area 23 consists of 5×5 pixel data. Numerical values of these pixel data indicate multi-value density levels.

Differential processing for the inspection image data shown in FIG. 4 using a differential operator Db in the y direction shown in FIG. 2B is as follows.

Of the pixel data 21 shown in FIG. 4, a differential value in the y direction for each of central density levels "5" corresponds to the difference "4" between two pixel data "7" and "3" adjacent to the density level "5" in the y direction.

More specifically, this differential value represents a slope defined by neighboring pixel data in the differential direction, i.e., the y direction.

Therefore, the first and second differential circuits 3 and 7 calculate differential values in the above-mentioned four directions in units of pixel data.

For example, when the differential values in the four directions are calculated for each of all pixel data constituting image data, the relationship between a pattern (original image) of image data and the differential values is as follows.

More specifically, the original image has an edge in the y direction, as shown in FIG. 5. When this original image is differentiated in the respective directions, the differential value in the x direction assumes a maximum value, and the differential value in the y direction assumes a minimum value "0", as shown in FIG. 6.

Note that the differential values in the +45° and −45° directions assume small values as compared to the differential value in the x direction.

The original image includes a defect G near the edge, as shown in FIG. 7. The defect G projects in the x direction.

In the differential value in the x direction for this original image, a discontinuous portion is generated in the x direction at the position of the defect G, as shown in FIG. 8.

On the other hand, in the differential value in the y direction, a value other than "0" corresponding to the defect G is generated. In the ±45° directions, differential values resulting from the defect G are generated.

Therefore, as can be seen from a comparison between the differential results shown in FIGS. 6 and 8, the differential direction in which the differential value largely changes due to the presence of the defect G is the y direction.

If the original image shown in FIG. 5 is assumed to be reference image data and the original image shown in FIG. 7 is assumed to be inspection image data, of the differential values in the respective directions for the reference image data, the differential value in the y direction assumes a minimum value.

The minimum value direction detection circuit 8 receives the differential values (absolute values) in the respective directions from the second differential circuit 7, and detects the differential direction corresponding to the smallest one of the received differential values (the y direction in this case). The circuit 8 supplies the y direction to the selector 4.

The selector 4 receives the differential values in the four directions from the first differential circuit 3, selects the differential value in the y direction designated by the minimum value direction detection circuit 8 from the received differential values, and sends the differential value in the y direction to a defect judge circuit (discrimination circuit) 9.

The defect judge circuit 9 compares the input differential value with a predetermined threshold value, and when the differential value exceeds the threshold value, the circuit 9 determines that the pattern defect G is present in the pixel data corresponding to this differential value.

A direct comparison circuit 10 directly compares pixel data which are not differentiated.

The direct comparison circuit 10 calculates difference data between each pixel data in the inspection image data and the corresponding pixel data in the reference image data.

A defect judge circuit 11 compares each of the difference data from the direct comparison circuit 10 with a threshold value. When the difference data exceeds the threshold value, the defect judge circuit 11 determines that a pattern defect is present in this pixel data.

On the other hand, FIG. 9A shows a differential value for the uniform portion (FIG. 3A) at the position C input to the defect judge circuit 9. This uniform portion includes a defect Ga.

All the differential values, in the respective directions, of the reference image data of this uniform portion are "0" and are equal to each other. For example, a maximum value of differential values in the x and y directions is calculated. Then, the reference pattern is compared with the maximum value. Thus, the defect Ga included in the uniform portion can be clearly detected, subject to the following limitations.

In general, when a pattern defect is detected by comparing an inspection pattern and a reference pattern, the position or pattern coordinates of inspection image data and reference image data must be set to perfectly coincide with each other.

If the position or pattern coordinates of these data are shifted from each other, pixel data at different positions are compared with each other. With this comparison, a pattern defect cannot be clearly detected.

In order to prevent the false defect due to the position mismatch between the image data, the first and second differential circuits 3 and 7 compare differential values in the respective directions.

More specifically, inspection image data and reference image data are shifted by Δt in the x direction, as shown in FIG. 9B. In this case, even if no defect Gb is present at all, the entire area, in the vertical direction, of the width Δt is detected as a pattern defect as a result of defect detection of the direct comparison circuit 10.

When the reference image data and the inspection image data which are shifted by Δt from each other are differentiated in the respective directions, the differential value in the x direction changes at the edge portion of the pattern, but the differential value in the y direction does not change from "0".

Therefore, based on the differential value "0" in the y direction, even when the reference image data and the inspection image data are shifted by Δt from each other, the pattern edge portion is not detected as a defect.

On the other hand, when a defect Gb is present, as shown in FIG. 9B, the differential value, in the y direction, of the inspection image data assumes a value corresponding to the defect Gb. The defect judge circuit 9 detects a pattern defect from this differential value.

In this manner, even when the position or pattern coordinates of the inspection image data and the reference image data do not perfectly coincide with each other, a pattern defect is detected.

However, in the corner portion at the position B in FIG. 3, as shown in FIGS. 10A and 10B, a shift portion of the width Δt is detected as a false defect Gc.

More specifically, in the corner portion, the differential values in the −45° direction have some small value, and the differential values in the remaining directions has bigger value.

If the position or pattern coordinates are shifted from each other, the minimum differential value directions of the inspection image data and the reference image data with respect to pixel data do not coincide with each other.

As a result, although the selector 4 selects the differential value in the differential direction designated by the minimum value direction detection circuit 8, the selected differential value is not "0" but has a value corresponding to the shift width Δt.

Therefore, when this differential value exceeds a threshold value, the defect judge circuit 9 detects a pattern defect.

On the other hand, when the corner portion includes a defect Gd, as shown in FIG. 10B, the differential value corresponding to this defect Gd is selected by the selector 4. The defect judge circuit 9 detects the differential value corresponding to this defect Gd as a pattern defect Ge.

For this reason, the pattern defect Ge resulting from the defect Gd is detected in the same manner as the false defect Gc due to the shift width Δt.

Therefore, whether the defect Gd is actually present sent or the pattern defect Gc is detected due to the position mismatch cannot be distinguished from each other.

SUMMARY OF THE INVENTION

It is an object of the present invention to provide a pattern defect inspection method, which can accurately detect only a pattern defect even when the position or pattern coordinates of inspection image data and reference image data are slightly shifted from each other, and can improve defect detection accuracy and defect detection reliability.

It is another object of the present invention to provide a pattern defect inspection apparatus, which can accurately detect only a pattern defect even when the position or pattern coordinates of inspection image data and reference image data are slightly shifted from each other, and can improve defect detection accuracy and defect detection reliability.

According to the present invention, a pattern edge direction in reference image data for pattern defect detection of an object to be inspected is detected, reference image data is differentiated using a differential operator in a direction along the detected pattern edge direction, and inspection image data obtained by scanning an image of the object to be inspected is differentiated using the differential operator in the direction along the detected pattern edge direction. The differential data obtained by the differential processing are compared with the inspection image data, and a pattern defect on the object to be inspected is detected on the basis of the difference between these data.

According to the present invention, there is provided a pattern defect inspection apparatus comprising: image pickup means for picking up an image of an object to be inspected to generate inspection image data; reference image generation means for generating reference image data for comparing with the inspecting pattern on the object; edge direction detection means for detecting a pattern edge direction in the reference image data; first edge direction differential means for executing differential processing of the inspection image data using a differential operator in a direction along the pattern edge direction; second edge direction differential means for executing differential processing of the reference image data using the differential operator in the direction along the pattern edge direction; differential processing means for executing differential processing of surrounding pixels in the reference image data using the differential operator in the direction along the pattern edge direction, and executing differential processing of the reference image data using differential operators in directions neighboring the pattern edge direction; and discrimination means for detecting a pattern defect of the object to be inspected on the basis of a difference between difference data obtained by the first edge direction differential means, and differential data obtained by the second edge direction differential means or at least one of differential data obtained by the differential processing means.

According to the above-mentioned apparatus, inspection image data is generated by scanning an image of an object to be inspected, and reference image data of the object to be inspected is generated. Of these data, a pattern edge direction in the reference image data is detected. The inspection image data is differentiated using a differential operator along the detected pattern edge direction, and the reference image data is also differentiated using the differential operator along the detected pattern edge direction. Furthermore, surrounding pixels of the reference image data are differentiated using a differential operator in a direction along the pattern edge direction, and are differentiated using differential operators in directions neighboring the pattern edge direction, each such neighboring direction hereinafter being called an adjacent direction of the edge direction. Then, a pattern defect of the object to be inspected is discriminated on the basis of the difference between the differential value for the inspection image data and at least one differential value of those for the reference image data.

BRIEF DESCRIPTION OF THE DRAWINGS

FIG. 3 is a view showing inspection image data corresponding to edge, corner, and uniform portions;

FIG. 4 is a view showing the inspection image data of the edge portion;

FIG. 5 is a view showing an original image without a defect;

FIG. 6 is a view showing the differential values of the original image;

FIG. 12 is a view showing differential results in respective differential directions;

FIG. 13A is a view showing the differential direction and differential value of an edge portion;

FIG. 13B is a view showing the differential direction and differential value of a corner portion;

FIG. 13C is a view showing the differential direction and differential value of a uniform portion;

FIG. 15 is a block diagram showing a pattern defect inspection apparatus according to an embodiment of the present invention;

FIG. 18 is a view showing the density values of the edge, corner, and uniform portions in the reference image data;

FIG. 19 is a view showing inspection image data without a defect;

FIG. 20 is a view showing the density values of edge, corner, and uniform portions in the inspection image data;

FIG. 25A is a view showing the differential value, in the edge direction, of the reference image data;

FIG. 25B is a view showing the maximum differential value of surrounding pixels of the reference image data;

FIG. 25C is a view showing the maximum differential values, in adjacent directions, of the reference image data;

FIG. 26A is a view showing the subtraction result, in the edge direction, of the inspection image data without a defect;

FIG. 26B is a view showing the subtraction result of surrounding pixels of the inspection image data without a defect;

FIG. 26C is a view showing the subtraction result, in adjacent directions, of the inspection image data without a defect;

FIG. 27A is a view showing the subtraction result, in the edge direction, of the inspection image data with a defect;

FIG. 27B is a view showing the subtraction result of surrounding pixels of the inspection image data with a defect;

FIG. 27C is a view showing the subtraction result, in adjacent directions, of the inspection image data with a defect;

FIG. 28 is a view showing the edge direction of the reference image data;

FIG. 29A is a view showing the differential value of the inspection image data without a defect;

FIG. 29B is a view showing the differential value of the inspection image data with a defect;

FIG. 30A is a view showing the differential value, in the edge direction, of the reference image data;

FIG. 30B is a view showing the differential value of surrounding pixels of the maximum reference image data;

FIG. 30C is a view showing the maximum differential value, in neighboring directions, of the reference image data;

FIG. 31A is a view showing the subtraction result, in the edge direction, of the inspection image data without a defect;

FIG. 31B is a view showing the subtraction result of surrounding pixels of the inspection image data without a defect;

FIG. 31C is a view showing the subtraction result, in adjacent directions, of the inspection image data without a defect;

FIG. 32A is a view showing the subtraction result, in the edge direction, of the inspection image data with a defect;

FIG. 32B is a view showing the subtraction result of surrounding pixels of the inspection image data with a defect;

FIG. 32C is a view showing the subtraction result, in adjacent directions, of the inspection image data with a defect;

FIG. 33A is a view showing the edge direction of the inspection image data without a defect;

FIG. 33B is a view showing the edge direction of the inspection image data with a defect;

FIG. 34A is a view showing the differential value of the inspection image data without a defect;

FIG. 34B is a view showing the differential value of the inspection image data with a defect;

FIG. 35A is a view showing the differential value, in the edge direction, of the reference image data;

FIG. 35B is a view showing the maximum differential value of surrounding pixels of the reference image data;

FIG. 35C is a view showing the maximum differential value, in adjacent directions, of the reference image data;

FIG. 36 is a view showing the subtraction result without a defect;

FIG. 37 is a view showing the subtraction result with a defect;

FIG. 38A is a view showing other differential operators in the x direction;

FIG. 38B is a view showing other differential operators in the y direction;

FIG. 38C is a view showing other differential operators in the +45° direction; and FIG. 38D other differential operators in the −45° direction.

DETAILED DESCRIPTION OF THE PREFERRED EMBODIMENTS

Prior to the description of an embodiment of the present invention, a pattern defect inspection apparatus as a premise of the embodiment will be described below.

Figure 11:
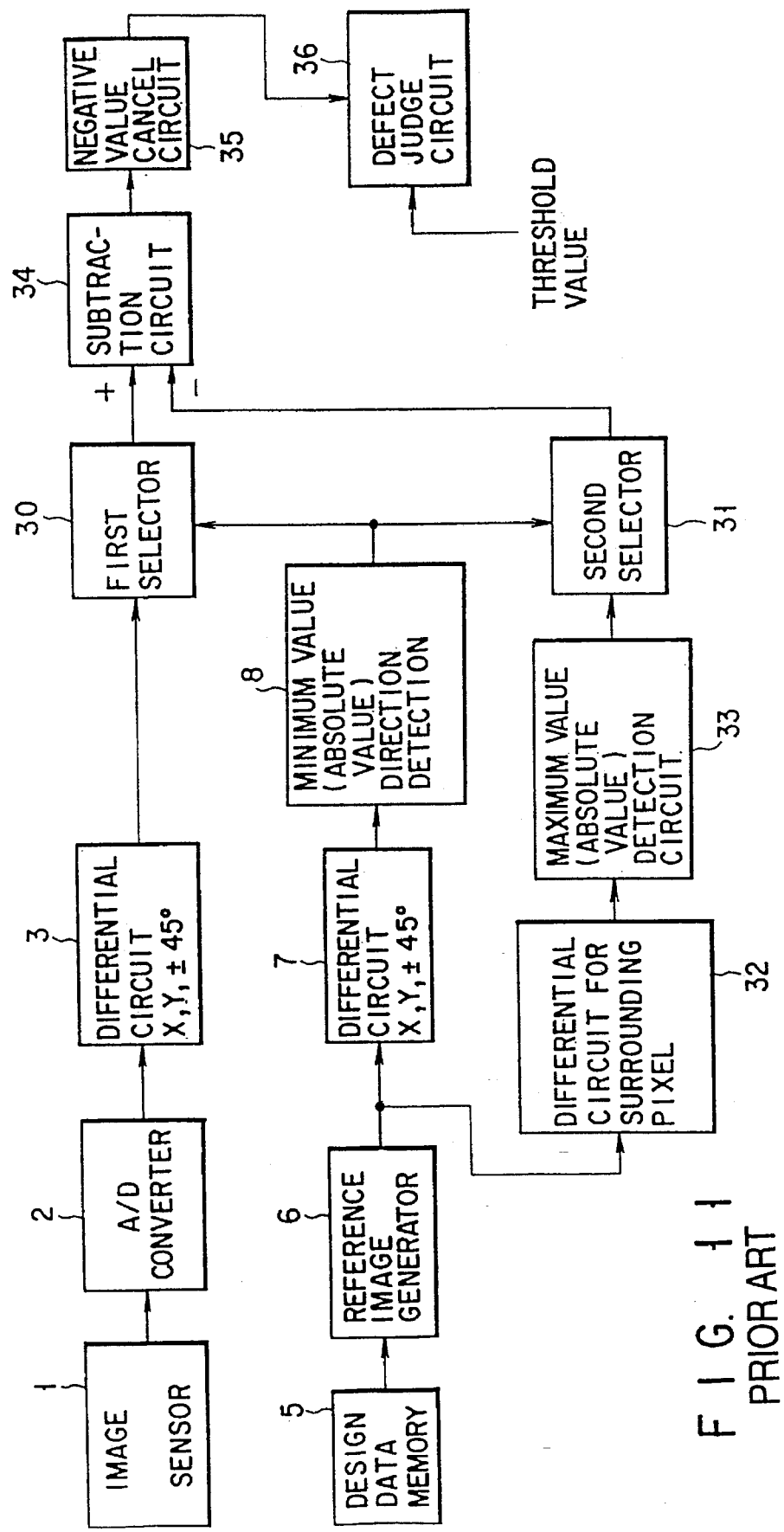
FIG. 11 is a block diagram showing the arrangement of a pattern defect inspection apparatus that is prior art for the present invention.

FIG. 11 is a block diagram showing the arrangement of the pattern defect inspection apparatus. The same reference numerals in FIG. 11 denote the same parts as in the pattern defect inspection apparatus shown in FIG. 1. Therefore, a detailed description of repetitive portions will be omitted.

An image signal output from an image sensor (for instance scan) 1 is converted into multi-value data by an A/D converter 2, and thereafter, the multi-value data is spatially differentiated by a first differential circuit 3 using differential operators in the x, y, and ±45° directions.

On the other hand, a design pattern output from a design data memory 5 is converted into reference image data by a reference image generator 6, and thereafter, the reference image data is spatially converted by a second differential circuit 7 using differential operators in the x, y, and ±45° directions.

A minimum value direction detection circuit 8 detects a differential direction corresponding to a differential value having the smallest absolute value of the differential values output from the second differential circuit 7, and sends this differential direction to first and second selectors 30 and 31.

On the other hand, the reference image data output from the reference image generator 6 is supplied to a third differential circuit 32.

Corresponding to the input timing of one pixel data of interest to the second differential circuit 7, the third differential circuit 32 fetches 3×3, i.e., a total of nine pixel data forming a local area including the pixel data of interest at the center.

The third differential circuit 32 calculates differential values for eight surrounding pixel data and the central pixel data other than the central pixel data of the fetched pixel data using the differential operators in the four directions.

The nine differential values in nine direction output from the third differential circuit 32 are input to a maximum value detection circuit 33.

The maximum value detection circuit 33 detects a maximum differential value, i.e., a differential value having the largest absolute value in each direction from the eight differential values in each direction output from the third differential circuit 32, and supplies these four maximum differential values to the second selector 31.

The first selector 30 selects a differential value in the differential direction designated by the minimum value direction detection circuit 8 from the differential values in the four directions output from the first differential circuit 3, and outputs the selected value to a subtraction circuit 34.

The second selector 31 selects a maximum differential value in the differential direction designated by the minimum value direction detection circuit 8 from the four maximum differential values input from the maximum value detection circuit 33, and outputs the selected value to the subtraction circuit 34.

The subtraction circuit 34 calculates the difference between the differential value from the first selector 30 and the maximum differential value from the second selector 31, and supplies the difference as a difference differential value to a negative value cancel circuit 35.

The negative value cancel circuit 35 replaces only a negative difference differential value by "0", and supplies the difference differential value to a defect judge circuit 36.

When the difference differential value exceeds a predetermined threshold value, the defect judge circuit 36 determines that pixel data corresponding to the difference differential value is a pattern defect.

An operation after the first to third differential circuits 3, 7, and 32 will be described in detail below.

An operation for central pixel data "5" in a local area 23 of an edge portion at a position A shown in FIG. 3 is as follows.

The first differential circuit 3 fetches, e.g., nine pixel data in the local area 23 including the central pixel data "5" at the center.

The first differential circuit 3 calculates differential values, in the four directions, of the central pixel data "5".

The first differential circuit 3 performs spatial differentiation using differential operators Da to Dd in the x, y, and ±45° directions.

Similarly, the second differential circuit 7 spatially differentiates pixel data of reference image data using the differential operators Da to Dd in the four directions to obtain differential values. Therefore, differential values 37a to 37d, in the four directions, for the central pixel data "5" are respectively "0", "4", "4", and "−4", as shown in FIG. 12.

The absolute values of differential values 37a to 37d at the position A in the reference image data shown in FIG. 12 are respectively "0", "4", "4", and "4". The minimum value is "0".

The minimum value direction detection circuit 8 supplies the x direction corresponding to the differential value 37a having the minimum value "0" to the first and second selectors 30 and 31.

The third differential circuit 21 calculates differential values 38 in the four directions for each of the eight pixel data and central pixel data spatially differentiated by the second differential circuit 7.

All the differential values in the x direction for eight surrounding pixel data and the central pixel data around the central pixel data "5" at the position A are "0", as shown in FIG. 12.

The differential values in the y direction include six "5"'s and three "4"'s. The differential values in the ±45° direction include six "5"'s and three "4"'s. The differential values in the −45° direction include six "−5"'s and three "−4"'s.

Therefore, the maximum values of the absolute values of these differential values in the four directions are respectively "0", "5", "5", and "5".

Since the minimum value direction detection circuit 8 selects the x direction for the edge portion at the position A, the maximum differential value selected by the second selector 31 is "0" shown in FIG. 13A.

If neither a defect nor a coordinate shift are present, the first selector 30 selects the value "0" of the differential value 37a in the x direction for the central pixel data "5".

As a result, the subtraction circuit 34 outputs a difference differential value "0". In this case, the defect judge circuit 36 does not detect any pattern defect, as a matter of course.

FIG. 13B shows the processing result for central pixel data "6" in a corner portion at a position B. In this case, the minimum value direction of the differential values in the four directions of the pixel data "6" is the −45° direction.

A differential value of pixel data in the −45° direction becomes "0", and nine differential values in the −45° direction of surrounding pixel data and the central pixel data include values "4", "3", "2", and "0". Therefore, the maximum value is "4".

In this case, a difference differential value output from the subtraction circuit 34 is "−4", and the negative cancel circuit 35 replaces the difference differential value "−4" by "0".

Therefore, the defect judge circuit 36 does not detect any pattern defect.

FIG. 13C shows the processing result for central pixel data "0" in a uniform portion at a position C. In this case as well, no pattern defect is output.

A case will be explained below wherein no defect is present, and the position or pattern coordinates of inspection image data and reference image data are shifted from each other by about one pixel.

The minimum value direction detection circuit 8 detects the x direction for the edge portion at the position A shown in FIG. 3. The subtraction circuit 34 receives a differential value "0" in the x direction from the first differential circuit 3.

Similarly, a differential value in the x direction of surrounding pixel data becomes "0", and no pattern defect is output.

Then, a differential value in the −45° direction for central pixel data in the corner portion at the position B shown in FIG. 3 in the inspection image data becomes "0". Differential values in other directions have constant values determined by the differential directions.

On the other hand, central pixel data in the reference image data does not correspond to the central pixel data in the inspection image data, and is shifted by one pixel from it.

Therefore, a differential value in the −45° direction for the shifted pixel data exhibits a value which is not "0".

As a result, the minimum value direction detection circuit 8 does not always designate the −45° differential direction. Therefore, the first selector 30 does not always select the differential value "0" in the −45° direction.

Figure 14A:
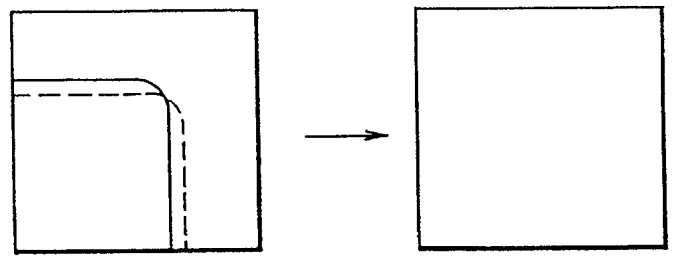
FIG. 14A is a view showing the comparison result of a normal corner portion.

On the other hand, in the reference image data, the minimum value direction detection circuit 8 detects a value at least larger than the differential value output from the first selector 30. As a result, the subtraction circuit 34 calculates the difference between the values from the selectors 30 and 31. With this calculation, the differential value output from the first selector 30 is canceled. Therefore, no defect is output, as shown in FIG. 14A.

A case will be explained below wherein a defect is present, and the position or pattern coordinates of inspection image data and reference image data are shifted from each other by about one pixel.

For the local area 23 of the edge portion at the position A, the first differential circuit 3 differentiates inspection image data, and outputs a differential value in the x direction corresponding to the defect.

In contrast to this, the second differential circuit 7 outputs a differential value "0" in the x direction of surrounding pixel data around the central pixel data.

As a result, the subtraction circuit 34 outputs a difference differential value corresponding to the defect scale. The defect judge circuit 36 outputs a pattern defect.

The differential direction designated by the minimum value direction detection circuit 8 for the local area 23 of the corner portion at the position B, is not uniquely determined.

The first differential circuit 3 outputs differential values corresponding to the defect in the respective differential direction including the −45° direction.

The first selector 30 selects a differential value corresponding to the defect.

Figure 14B:
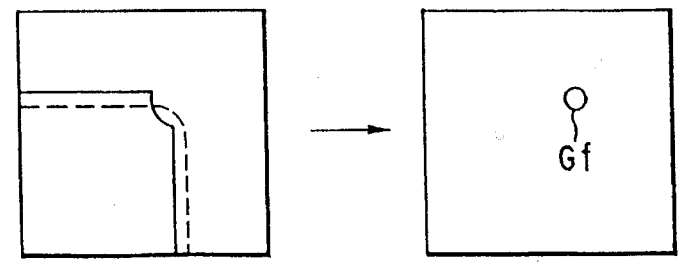
FIG. 14B is a view showing the comparison result of a corner portion with a defect.

On the other hand, values in the respective differential directions obtained by differentiating the surrounding pixels in the reference image data by the third differential circuit 32 do not correspond to the values caused by the presence of the defect at all. Therefore, the subtraction circuit 34 detects a defect Gf, as shown in FIG. 14B.

Therefore, even when the coordinate system of the inspection image data and the reference image data are slightly shifted from each other, the defect Gf can be prevented from including a pseudo defect Gc caused by the shift, and only an actual defect can be reliably detected with high accuracy.

An embodiment of the present invention will be described below.

FIG. 15 is a block diagram showing the arrangement of a pattern defect detection apparatus.

An image sensor 40 comprises a line sensor. The image sensor 40 is connected to a plural direction differential circuit 42 via an A/D converter 41.

The plural direction differential circuit 42 has differential operators in the x, y, +45°, and −45° directions, and has a function of executing differential processing of inspection image data using these differential operators.

Note that this plural direction differential circuit 42 has differential operators in +22.5°, +67.5°, −22.5°, and −67.5° directions shown in FIG. 16 in addition to the above-mentioned differential operators.

Therefore, the plural direction differential circuit 42 has a function of executing differential processing of inspection image data in the four or eight directions of these differential operators.

A maximum value direction detection circuit 43 has a function of receiving processing results in the respective differential directions from the plural direction differential circuit 42, detecting the differential direction of a differential value having a maximum value from the received differential values (absolute values) in the respective differential directions, and supplying the detected differential direction to a selector 44.

On the other hand, a reference data generation circuit 45 has a function of generating reference image data corresponding to inspection image data obtained by an image pickup operation of the image sensor on the basis of design data of pattern data in synchronism with position data.

An edge direction detection circuit 46 has a function of detecting edge directions of the pattern in the reference image data in units of pixels, and supplying the detection results to the selector 44.

when the pattern edge direction is undecidable, the edge direction detection circuit 46 has a function of sending a message indicating that the direction is indefinite to the selector 44.

The selector 44 has a function of normally selecting the differential direction detected by the edge direction detection circuit 46 as a edge direction, and selecting the differential direction detected by the maximum value direction detection circuit 43 upon reception of a message indicating that the direction is indefinite.

A first edge direction differential circuit 47 has a function of receiving the differential direction as the edge direction selected by the selector 44, and executing differential processing of inspection image data from the A/D converter 41 using the received differential direction so as to calculate the absolute value of the differential value.

On the other hand, a second edge direction differential circuit 48 has a function of receiving the differential direction as the edge direction selected by the selector 44, and executing differential processing of reference image data using the received differential direction so as to calculate the absolute value of the differential value.

A differential processing means 50 has a function of executing differential processing of surrounding pixels and the central pixel of the reference image data using differential operators for edge direction.

Also, the differential processing means 50 has a function of executing differential processing of the reference image data using differential operators in the adjacent direction of the edge direction.

More specifically, the differential processing means 50 has functions of a surrounding pixel edge differential circuit 51, a first maximum value detection circuit 52, a adjacent direction differential circuit 53, and a second maximum value detection circuit 54.

The surrounding pixel differential circuit 51 has a function of executing differential processing of reference image data for surrounding pixels and the central pixel, for which a differential value is to be calculated, using a differential operator for the edge direction detected by the edge direction detection circuit 46.

The first maximum value detection circuit 52 has a function of detecting a maximum absolute value from the differential values of the surrounding pixels calculated by the surrounding pixel differential circuit 51.

The adjacent direction differential circuit 53 has a function of executing differential processing of reference image data using differential operators in directions neighboring the pattern edge direction detected by the edge direction detection circuit 46.

The adjacent direction differential circuit 53 has a function of executing differential processing of reference image data using differential operators in the x and y directions which are orthogonal to each other, and the ±45°, ±22.5°, and ±67.5° directions with respect to the x direction.

The second maximum value detection circuit 54 has a function of detecting a maximum absolute value from the values of the differential values calculated by the adjacent direction differential circuit 53.

The outputs of the edge direction differential circuit 48 and the first and second maximum value detection circuits 52 and 54 are connected to a subtraction circuit 56 via a select switch 55.

The subtraction circuit 56 has a function of calculating the differences, in units of pixels, between the inspection image data differentiated by the edge direction differential circuit 47, and differential data from one of the edge direction differential circuit 48, and the first and second maximum value detection circuits 52 and 54, which is selected by the select switch 55.

A defect judge circuit 57 has a function of comparing difference values in units of pixels from the subtraction circuit 56 with a predetermined threshold value, and determining, to be a defect, a pixel corresponding to the difference value in units of pixels, which exceeds the threshold value.

The operation of the apparatus with the abovementioned arrangement will be described below.

The reference data generation circuit 45 generates reference image data on the basis of design data of the pattern to be formed on the inspected object.

Figures 16A, 16B, 16C, 16D, 17:
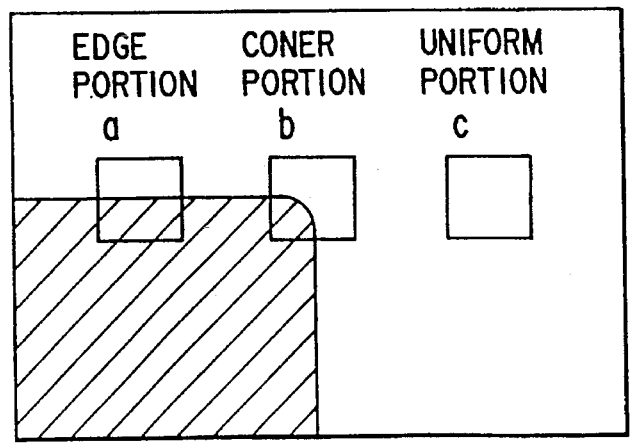
FIG. 16A is a view showing a differential operator in the +22.5° direction.
FIG. 16B is a view showing a differential operator in the +67.5° direction.
FIG. 16C is a view showing a differential operator in the −22.5° direction.
FIG. 16D is a view showing a differential operator in the −67.5° direction.
FIG. 17 is a view showing reference image data including edge, corner, and uniform portions.

FIG. 17 is a view showing the reference image data. Local areas, edge, corner, and uniform portions a, b, and c are set. Each of these edge, corner, and uniform portions a, b, and c is defined by 7×7 pixels, as shown in FIG. 18. In each of the edge, corner, and uniform portions a, b, and c, a dark portion is indicated by a density level "0", and a light portion is indicated by a density level "10".

In this manner, the reference image data is data generated based on the design data, and has smooth density gradation at an edge.

On the other hand, the image sensor 40 continuously picks up an image of an object to be inspected, and outputs its image signal. The image signal is converted into digital inspection image data corresponding to 11 density levels by the A/D converter 41.

FIG. 19 is a view showing inspection image data without a defect. Each of the edge, corner, and uniform portions a, b, and c in the inspection image data is defined by 5×5 pixels, as shown in FIG. 20.

Figures 21, 22, 23, 24A, 24B:
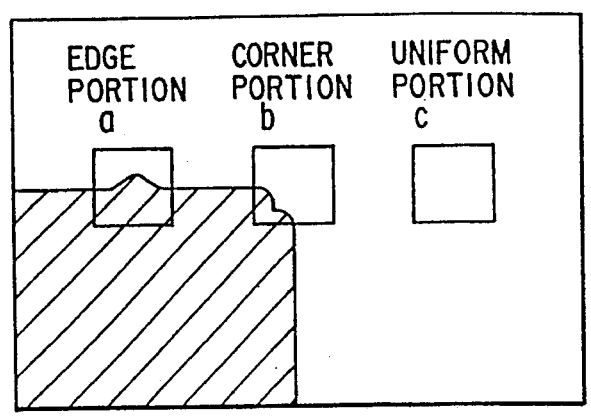
FIG. 21 is a view showing inspection image data with a defect.
FIG. 22 is a view showing the density values of edge, corner, and uniform portions in the inspection image data with a defect.
FIG. 23 is a view showing the edge direction of the reference image data.
FIG. 24A is a view showing the differential value of the inspection image data without a defect.
FIG. 24B is a view showing the differential value of the inspection image data with a defect.

FIG. 21 is a view showing inspection image data with a defect. Each of the edge, corner, and uniform portions a, b, and c in the inspection image data is defined by 5×5 pixels, as shown in FIG. 22.

Note that a noise component of level "1" is superposed on these inspection image data due to, e.g., a sampling error of the image sensor 40 and A/D converter 41.

Image data of each corner portion b in these inspection image data is shifted by one pixel from image data of the corner portion b shown in FIG. 18 in the −y direction.

When these reference and inspection image data are obtained, the reference image data is supplied to the edge direction detection circuit 46.

The edge direction detection circuit 46 performs differential processing of the reference image data in the x, y, +45°, and −45° directions, and detects the differential direction of a minimum differential value from the calculated differential values.

(a) Processing for the edge portions a in the reference and inspection image data will be described below.

The pattern edge direction in the edge portion a of the reference image data corresponds to the differential direction of the x direction, as shown in FIG. 23.

Therefore, the selector 44 selects the differential direction x, and sends it to the first and second edge direction differential circuits 47 and 48, the surrounding pixel edge direction differential circuit 51, and the neighboring direction differential circuit 53.

The first edge direction differential circuit 47 executes differential processing of the inspection image data using differential operators in the x direction.

When pixels in the edge portion a without a defect shown in FIG. 20 are differentiated in the x direction, the absolute values of differential processing values without a defect shown in FIG. 24A are obtained.

When pixels in the edge portion a with a defect shown in FIG. 22 are differentiated in the x direction, the absolute values of differential processing values with a defect shown in FIG. 24B are obtained.

The inspection image data differentiated by the first edge direction differential circuit 47 is supplied to the subtraction circuit 56.

Figures 1, 2A, 2B, 2C, 2D:
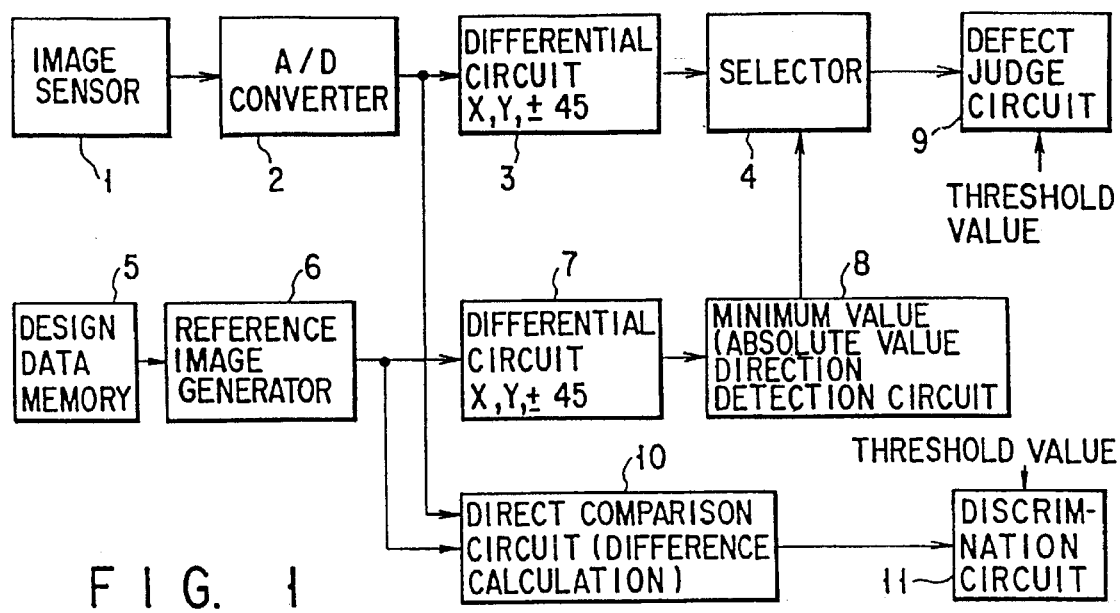
FIG. 1 is a block diagram showing the arrangement of a conventional pattern defect detection apparatus.
FIG. 2A is a view showing a differential operator in the x direction.
FIG. 2B is a view showing a differential operator in the y direction.
FIG. 2C is a view showing a differential operator in the +45° direction.
FIG. 2D is a view showing a differential operator in the −45° direction.
Figure 7:
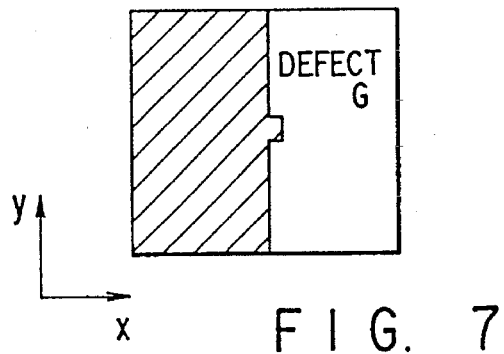
FIG. 7 is a view showing an original image with a defect.
Figure 8A:
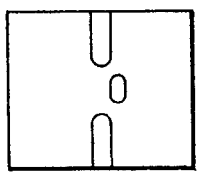
FIG. 8 is a view showing the differential values of the original image.
Figure 8B:
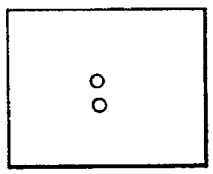
Figure 8C:
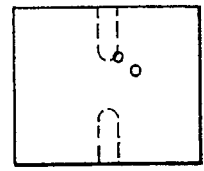
Figure 8D:
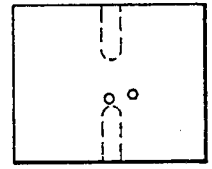
Figure 9A:
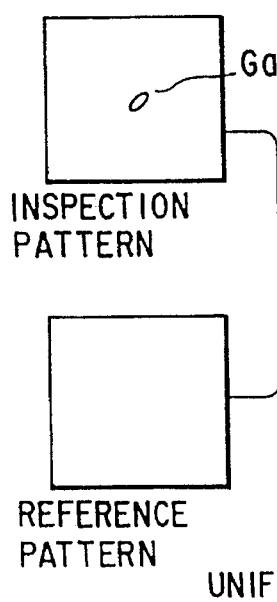
FIG. 9A is a view showing the defect detection result of the uniform portion when a coordinate shift occurs.
Figure 9B:
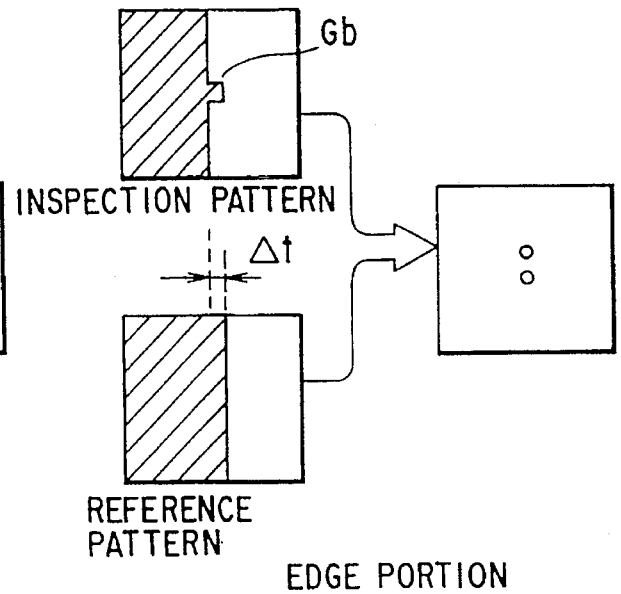
FIG. 9B is a view showing the defect detection result of the edge portion when a coordinate shift occurs.
Figure 10A:
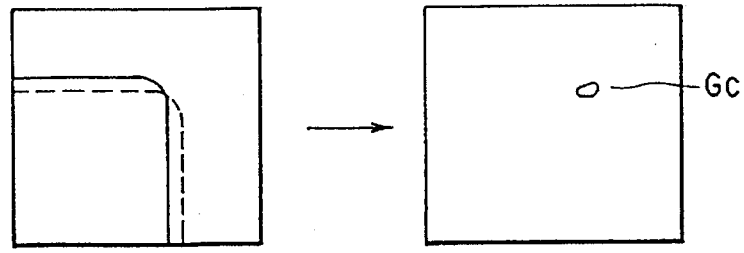
FIG. 10A is a view showing the defect detection result of a corner portion when a coordinate shift occurs.
Figure 10B:
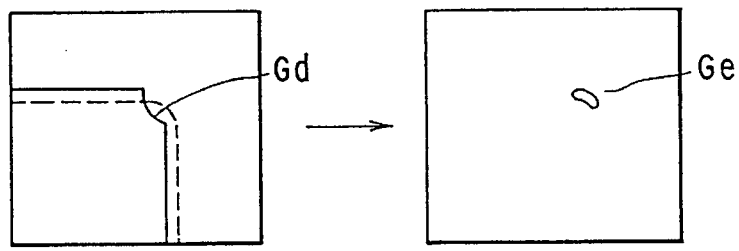
FIG. 10B is a view showing the defect detection result of a corner portion with a defect when a coordinate shift occurs.

On the other hand, the second edge direction differential circuit 48 executes differential processing of the edge portion a of the reference image data using differential operators in the x direction shown in FIG. 2A so as to obtain the absolute values of the differential values. The differential result is as shown in FIG. 25A.

More specifically, in the edge portion a of the reference image data, pixel data, in the x direction, above central pixel data "5" have values "8", "8", "8", . . . , as shown in FIG. 18.

Pixel data in the x direction passing the central pixel data "5" have values "5", "5", "5", . . . .

Pixel data, in the x direction, below the central pixel data "5" have values "2", "2", "2", . . . .

Therefore, all differential values, in the x direction, for these pixel data are "0", as shown in FIG. 25A.

The surrounding pixel edge direction differential circuit 51 executes differential processing of surrounding pixels around the central pixel data "5" in the edge portion a.

First, differential values, in the x direction, for surrounding pixels around upper left pixel data "8" with respect to the central pixel data "5" in the edge portion a shown in FIG. 18 are calculated.

The surrounding pixels around the pixel data "8" are, in turn from the upper left pixel in the clockwise direction, "10", "10", "10", "8", "5", "5", "5" and "8" and the upper left pixel again "10" appears again.

Therefore, the surrounding pixel edge direction differential circuit 51 calculates differential values, in the x direction, of these surrounding pixels.

The maximum value detection circuit 52 detects a maximum value "0" from the absolute values of the differential values in the x direction calculated by the surrounding pixel edge direction differential circuit 51.

The maximum value "0" detected by the maximum value detection circuit 52 becomes a differential value for the upper left pixel data "8" with respect to the central pixel data "5" in the edge portion a.

Then, differential values, in the x direction, for surrounding pixels around upper pixel data "8" of the central pixel data "5" in the edge portion a are calculated.

The surrounding pixels around this pixel data "8" are, in turn from the upper left pixel in the clockwise direction, "10", "10", "10", "8", "5", "5", "5", and "8", and the upper left pixel "10" appears again.

Therefore, the surrounding pixel edge direction differential circuit 51 calculates differential values, in the x direction, of these surrounding pixels.

The maximum value detection circuit 52 detects a maximum value "0" from the absolute values of the differential values in the x direction calculated by the surrounding pixel edge direction differential circuit 51.

The maximum value "0" detected by the maximum value detection circuit 52 becomes a differential value for the upper pixel data "8" of the central pixel data "5" in the edge portion a.

Similarly, the surrounding pixel edge direction differential circuit 51 calculates differential values for each of surrounding pixels around the central pixel data "5" in the edge portion a.

FIG. 25B shows the differential results of the surrounding pixel edge direction differential circuit 51.

The neighboring direction differential circuit 53 executes differential processing of the reference image data using differential operators in directions neighboring the x direction as the pattern edge direction, i.e., in the ±22.5° directions shown in FIG. 16.

More specifically, differential values, in the ±22.5° direction, for the upper left, upper, and upper right pixel data "8" with respect to the central pixel data "5" of the reference image data are "2". Digits below the decimal point are dropped.

Similarly, differential values, in the −22.5° direction, for the upper left, upper, and upper right pixel data "8" are "−2".

Therefore, the maximum value detection circuit 54 detects a maximum value "2" from the absolute values of the differential values "2", "2", "2", "−2", "−2", and "2" of the upper left, upper, and upper right pixel data "8" with respect to the central pixel data "5" in the reference image data.

On the other hand, differential values, in the +22.5° direction, for the left, central, and right pixel data "5" with respect to the central pixel data "5" in the reference image data are "3".

Similarly, differential values, in the −22.5° direction, for the left, central, and right pixel data "5" are "−3".

Therefore, the maximum value detection circuit 54 detects a maximum value "3" from the absolute values of the differential values "3", "3", "3", "−3", "−3", and "−3" of the left, central, and right pixel data "5" with respect to the central pixel data "5" in the reference image data.

Also, differential values, the +22.5x direction, for the lower left, lower, and lower right pixel data "2" with respect to the central pixel data "5" in the reference image data are "2".

Similarly, differential values, in the −22.5° direction, for the lower left, lower, and lower right pixel data "2" are "2".

Therefore, the maximum value detection circuit 54 detects a maximum value "2" from the absolute values of the differential values "2", "2", "2", "−2", "−2", and "−2" of the lower left, lower, and lower right pixel data "2" with respect to the central pixel data "5" in the reference image data.

As a result, the differential values, the neighboring directions, for the reference image data are obtained, as shown in FIG. 25C.

These differential results of the second edge direction differential circuit 48, the surrounding pixel edge direction differential circuit 51, and the neighboring direction differential circuit 53 are supplied to the subtraction circuit 56 via the select switch 55.

The subtraction circuit 56 subtracts the differential results (FIGS. 25A, 25B, and 25C) of each of the second edge direction differential circuit 48, the surrounding pixel edge direction differential circuit 51, and the neighboring direction differential circuit 53 from the differential results (FIG. 24A or 24B) of the first edge direction differential circuit 47.

The subtraction results are supplied to the defect judge circuit 57.

When a negative value is obtained as a result of the subtraction, the corresponding subtraction result is set to be "0".

For example, when the differential values in the edge direction, the differential values in the surrounding pixel edge direction, and the differential values in the neighboring directions shown in FIGS. 25A, 25B, and 25C are respectively subtracted from the differential values of the inspection image data without a defect shown in FIG. 24A, the subtraction results are as shown in FIGS. 26A, 26B, and 26C, respectively.

On the other hand, when the differential values in the edge direction, the differential values in the surrounding pixel edge direction, and the differential values in the neighboring directions shown in FIGS. 25A, 25B, and 25C are respectively subtracted from the differential values of the inspection image data with a defect shown in FIG. 24B, the subtraction results are as shown in FIGS. 27A, 27B, and 27C, respectively.

More specifically, the subtraction results shown in FIGS. 26A to 26C and FIGS. 27A to 27C represent the differences between the inspection image data and the reference image data.

Therefore, pixel portions which do not coincide with each other between these image data are detected as a defect portion.

When the results from the subtraction circuit 56 are compared with a threshold value by the defect Judge circuit 57, a pattern defect is discriminated.

(b) Processing for the corner portions b in the reference and inspection image data will be described below.

The edge direction detection circuit 46 detects pattern edge directions in the corner portion b in the reference image data, as shown in FIG. 28.

Therefore, the selector 44 selects differential directions in units of pixels, and sends them to the first and second edge direction differential circuits 47 and 48, the surrounding pixel edge direction differential circuit 51, and the neighboring direction differential circuit 53.

In this case, when a plurality of edge directions detected by the edge direction detection circuit 46 correspond to a minimum differential value for a certain pixel, the selector 44 determines one edge direction in accordance with the priority order of the y direction, x direction −45° direction, and +45° direction.

The first edge direction differential circuit 47 executes differential processing of the inspection image data using differential operators in the detected differential direction.

More specifically, when pixel data in the corner portion b without a defect shown in FIG. 20 are differentiated in units of pixels, the absolute values of differential processing results without a defect shown in FIG. 29A are obtained.

On the other hand, when pixel data in the corner portion b with a defect shown in FIG. 22 are differentiated in units of pixels, the absolute values of differential processing results with a defect shown in FIG. 29B are obtained.

The differential results of the first edge direction differential circuit 47 are supplied to the subtraction circuit 56.

On the other hand, the second edge direction differential circuit 48 executes differential processing of pixel data in the corner portion b of the reference image data using differential operators in the differential directions detected by the edge direction detection circuit 46 so as to obtain the absolute values of the differential values. The differential results are as shown in FIG. 30A.

The surrounding pixel edge direction differential circuit 51 executes differential processing of surrounding pixels in the corner portion b of the reference image data in units of pixels in the same manner as described above.

The maximum value detection circuit 52 detects a maximum value from the absolute values of the differential values of the surrounding pixel edge direction differential circuit 51.

FIG. 30B shows the detection result.

The neighboring direction differential circuit 53 executes differential processing of the reference image data in the edge direction and directions neighboring the edge direction in the same manner as described above, and the next maximum value detection circuit 31 detects a maximum absolute value. FIG. 30C shows the detection result.

The differential results of the second edge direction differential circuit 48, the surrounding pixel edge direction differential circuit 51, and the neighboring direction differential circuit 53 are supplied to the subtraction circuit 56 via the select switch 55.

The subtraction circuit 56 subtracts the differential results (FIGS. 30A, 30B, and 30C) of each of the second edge direction differential circuit 48, the surrounding pixel edge direction differential circuit 51, and the neighboring direction differential circuit 53 from the inspection image data (FIG. 29A or 29B) differentiated by the first edge direction differential circuit 47.

FIGS. 31A, 31B, and 31C respectively show the results obtained by subtracting the differential results (FIGS. 30A, 30B, and 30C) of each of the second edge direction differential circuit 48, the surrounding pixel edge direction differential circuit 51, and the neighboring direction differential circuit 53 from the inspection image data without a defect (FIG. 29A) differentiated by the first edge direction differential circuit 47.

FIGS. 32A, 32B, and 32C respectively show the results obtained by subtracting the differential results (FIGS. 30A, 30B, and 30C) of each of the second edge direction differential circuit 48, the surrounding pixel edge direction differential circuit 51, and the neighboring direction differential circuit 53 from the inspection image data with a defect (FIG. 29B) differentiated by the first edge direction differential circuit 47.

These subtraction results are supplied to the defect judge circuit 57.

The defect judge circuit 57 discriminates a pattern defect by comparing the subtraction results from the subtraction circuit 56 with a threshold value.

(c) Processing for the uniform portions c in the reference and inspection image data will be described below.

When an object to be inspected has no defect, the edge direction detection circuit 46 detects edge directions in the uniform portion c in the image data, as shown in FIG. 33A. In this case, since the density level is uniform, the direction becomes indefinite.

When an object to be inspection has a defect, the edge direction detection circuit 46 detects pattern edge directions in the uniform portion c in the image data, as shown in FIG. 33B.

The plural direction differential circuit 42 executes differential processing of inspection image data using differential operators in the x, y, +45°, and −45° directions.

Therefore, the selector 44 selects a differential direction exhibiting a maximum value from the differential values in the edge directions detected by the maximum value direction detection circuit 43.

The first edge direction differential circuit 47 executes differential processing of the inspection image data using the differential operators in the detected differential direction.

More specifically, when pixel data in the uniform portion c without a defect shown in FIG. 20 are differentiated in units of pixels, the absolute values of differential processing results without a defect shown in FIG. 34A are obtained.

On the other hand, when pixel data in the uniform portion c with a defect shown in FIG. 22 are differentiated in units of pixels, the absolute values of differential processing results without a defect shown in FIG. 34B are obtained.

The second edge direction differential circuit 48, the surrounding pixel edge direction differential circuit 51, and the neighboring direction differential circuit 53 respectively execute differential processing of reference image data in accordance with the selected edge directions.

The processing results of all pixels are "0", as shown in FIGS. 35A, 35B, and 35C.

Therefore, the subtraction results of the subtraction circuit 56 become the same as the differential values of the inspection image data, as shown in FIGS. 36 and 37.

In this manner, the defect judge circuit 57 discriminates a pattern defect by comparing the subtraction results from the subtraction circuit 56 with a threshold value.

As described above, according to the embodiment, a pattern defect can be reliably detected by comparing the reference and inspection image data.

In particular, since the apparatus has a function of detecting a maximum value by executing differential processing of the reference image data for each pixel and surrounding pixels around the pixel, and detecting a maximum value by executing differential processing of the reference image data in the edge direction and in directions neighboring the edge direction, even when the edge, corner, and uniform portions a, b, and c suffer a coordinate position shift from the pattern, a pattern defect can be detected with high accuracy in these portions.

Note that the present invention is not limited to the above embodiment, and various changes and modifications may be made within the spirit and scope of the invention.

For example, the subtraction circuit 56 may calculate the difference between the inspection image data differentiated by the first edge direction differential circuit 47 and differential image data obtained from at least one of the second edge direction differential circuit 48, the surrounding pixel edge direction differential processing circuit 51, and the neighboring direction differential circuit 53.

Note that as differential operators, differential values in the x, y, and ±45° directions may be obtained using Sobel operators, as shown in, e.g., FIGS. 38A to 38D.

What is claimed is:

1. A pattern defect inspection apparatus comprising:

image pickup means for picking up image data of an object to be inspected to generate inspection image data, the object having at least one edge;

reference image generation means for generating reference image data representing a reference image for comparing with the inspection image data of the object;

edge direction detection means for detecting an edge direction at an image point in the reference image data, the image point being arranged on any point of the reference image;

first edge direction differential means for executing differential processing at an image point in the inspection image data comparable to the image point in the reference image data using a differential operator for the edge direction detected by the edge direction detection means and outputting an absolute value of each differential datum obtained by the differential processing;

second edge direction differential means for executing differential processing at the image point in the reference image data using the differential operator for the edge direction and outputting an absolute value of each differential datum obtained by the differential processing;

differential processing means for executing differential processing at the image point and in pixels surrounding the image point in the reference image data using the differential operator for the edge direction and outputting differential data, and for executing differential processing at the image point in the reference image data using multiple differential operators whose differential directions are the edge direction, the clockwise adjacent direction of the edge direction, and the counterclockwise adjacent direction of the edge direction to provide differential data;

means for calculating the maximum absolute value from the differential data of the image point and of pixels surrounding the image point, and calculating a maximum absolute value from the differential data of the image point; and discrimination means for detecting a pattern defect of the object to be inspected on the basis of a difference between differential data obtained by said first edge direction differential means, and differential data obtained by said second edge direction differential means or one of the differential data obtained by said differential processing means.

2. The apparatus according to claim 1, wherein said edge direction detection means comprises:

first functional means for executing differential processing at the image point in the reference image data using differential operators in x and y directions which are orthogonal to each other, and ±45° directions with respect to the x direction and outputting the each absolute value of the differential data; and second functional means for determining a first differential direction corresponding to a minimum value of the absolute differential values obtained by said first functional means, as an edge direction, the edge direction being determined to be undecidable (or undetectable) if all the absolute values of the differential data are the same.

3. The apparatus according to claim 2, further comprising:

a plural direction differential circuit for executing plural differential operations at the comparable image point in the inspection image data using plural differential operators and outputting absolute values of data from the differential operations;

a maximum value direction detection circuit for detecting a second differential direction corresponding to a maximum value from the absolute values outputted by said plural direction differential circuit; and a selector for selecting the edge direction detected by said edge direction detection means or the second differential direction detected by the maximum value direction detection circuit, depending on whether the edge direction detected by the edge direction detection circuit is the first differential direction determined by the second functional means as the edge direction or is determined by the second functional means to be undecidable, respectively.

4. The apparatus according to claim 3, wherein said plural direction differential circuit executes differential processing of the inspection image data using differential operators in the x and y directions which are orthogonal to each other and in the ±45° directions with respect to the x direction.

5. The apparatus according to claim 1, wherein said differential processing means comprises:

a surrounding pixel differential circuit for executing differential processing at the image point and in pixels surrounding the image point of the reference image data using the differential operator with respect to the edge direction detected by said edge direction detection means to produce differential data; and wherein said means for calculating the maximum absolute value comprises a first maximum value detection circuit for detecting a maximum absolute value from the differential data of the image point and of the surrounding pixels calculated by said surrounding pixel differential circuit.

6. The apparatus according to claim 5, wherein said surrounding pixel differential circuit executes differential processing at the image point and in the surrounding pixels of the reference image data using differential operators with respect to respective differential directions that are either the x and y directions, which are orthogonal to each other, or the ±45° directions with respect to the x direction.

7. The apparatus according to claim 1, wherein said differential processing means comprises:

an adjacent direction differential circuit for executing differential processing at the image point in the reference image data using multiple differential operators with respect to respective differential directions that are the edge direction detected by said edge direction detection means, a clockwise adjacent direction of the detected edge direction, and a counterclockwise adjacent direction of the detected edge direction; and wherein said means for calculating the maximum absolute value comprises a second maximum value detection circuit for detecting a maximum absolute value from the differential data of the image point.

8. The apparatus according to claim 7, wherein said adjacent direction differential circuit executes differential processing at the image point in the reference image data using differential operators with respect to respective differential directions that are either the x and y directions, which are orthogonal to each other, or ±22.5° directions, or ±67.5° directions with respect to the x direction.

9. The apparatus according to claim 1, wherein said differential processing means comprises:

a surrounding pixel differential circuit for executing differential processing at the image point and in the surrounding pixels of the reference image data using a differential operator with respect to the edge direction detected by said edge direction detection means; and an adjacent direction differential circuit for executing differential processing at the image point in the reference image data using multiple differential operators with respect to respective differential directions that are the edge direction detected by said edge direction detection means, a clockwise adjacent direction of the detected edge direction, and a counterclockwise adjacent direction of the detected edge direction; and wherein said means for calculating the maximum absolute value comprises a first maximum value detection circuit for detecting a maximum absolute value from the differential data of the image point and of the surrounding pixels calculated by said surrounding pixel differential circuit; and a second maximum value detection circuit for detecting a maximum absolute value from the differential data of the image point calculated by said adjacent direction differential circuit.

10. The apparatus according to claim 9, wherein said surrounding pixel differential circuit executes differential processing at the image point and in the surrounding pixels of the reference image data using respective differential operators with respect to differential directions that are either the x and y directions, which are orthogonal to each other, or the ±45° directions with respect to the x direction.

11. The apparatus according to claim 9, wherein said adjacent direction differential circuit executes differential processing at the image point in the reference image data using differential operators with respect to respective differential directions that are either the x and y directions, which are orthogonal to each other, or ±22.5° directions, or ±67.5° directions with respect to the x direction.

12. The apparatus according to claim 1, wherein said discrimination means comprises:

a subtracting circuit for calculating a difference at the comparable image point between the absolute value of the differential data obtained by said first edge direction detection differential means, and the absolute value of the differential data obtained by said second edge direction differential detection means or one of the differential data obtained by said differential processing means; and a defect judging circuit for comparing the difference calculated by said subtraction circuit with a predetermined threshold value, and determining that the comparable image point for which the difference exceeds the threshold value is a pattern defect.

13. The apparatus according to claim 1, wherein said image pickup means comprises:

an image sensor for picking up the image data of the object to be inspected and outputting an image signal of a density level; and an A/D converter for converting the image signal output from said image sensor into digital multi-value inspection image data corresponding to the density level.

14. The apparatus according to claim 1, wherein said reference image generation means comprises means for generating, from design data of a pattern formed on the object to be inspected, the reference image data in correspondence to the inspection image data from the image pickup means, including means for synchronizing the design data with image data in respect to positions in the object to be inspected.

* * * * *

UNITED STATES PATENT AND TRADEMARK OFFICE
CERTIFICATE OF CORRECTION

PATENT NO. : 5,574,800
DATED : November 12, 1996
INVENTOR(S) : Hiromu INOUE et al.

It is certified that error appears in the above-indentified patent and that said Letters Patent is hereby corrected as shown below:

Claim 3, column 19, line 53, "direction-corresponding" should read --direction corresponding--.

Signed and Sealed this

Eighth Day of April, 1997

Attest:

BRUCE LEHMAN

*Attesting Officer*  *Commissioner of Patents and Trademarks*